US008211486B2

(12) United States Patent
Beers et al.

(10) Patent No.: US 8,211,486 B2
(45) Date of Patent: Jul. 3, 2012

(54) PROCESS FOR THE HYDROGENATION OF UNSATURATED TRIGLYCERIDES

(75) Inventors: Annemarie Elisa Wilhelmina Beers, Utrecht (NL); Pieter Hildegardus Berben, Maarn (NL)

(73) Assignee: BASF Corporation, Florham Park, NJ (US)

( * ) Notice: Subject to any disclaimer, the term of this patent is extended or adjusted under 35 U.S.C. 154(b) by 924 days.

(21) Appl. No.: 11/914,054

(22) PCT Filed: May 9, 2005

(86) PCT No.: PCT/NL2005/000347
§ 371 (c)(1),
(2), (4) Date: Jul. 21, 2008

(87) PCT Pub. No.: WO2006/121320
PCT Pub. Date: Nov. 16, 2006

(65) Prior Publication Data

US 2009/0142470 A1 Jun. 4, 2009

(51) Int. Cl.
*C07C 51/36* (2006.01)
*A23D 9/00* (2006.01)

(52) U.S. Cl. ........ 426/313; 502/150; 502/325; 502/173; 502/330; 502/344; 977/778; 977/779; 977/783; 554/141; 554/145; 554/146

(58) Field of Classification Search .................. 426/313; 554/141, 145, 146; 502/150, 325, 173, 330, 502/344; 977/778, 779, 783
See application file for complete search history.

(56) References Cited

U.S. PATENT DOCUMENTS

| | | | | |
|---|---|---|---|---|
| 2,329,934 | A | 9/1943 | Franz | |
| 5,734,070 | A * | 3/1998 | Tacke et al. | 554/144 |
| 6,090,746 | A | 7/2000 | Boennemann et al. | |
| 2008/0199582 | A1* | 8/2008 | Unger | 426/519 |

FOREIGN PATENT DOCUMENTS

| | | |
|---|---|---|
| EP | 0823473 | 2/1998 |
| EP | 1002578 | 5/2000 |
| RU | 2260037 | 9/2005 |
| WO | 2006094623 A1 | 9/2006 |

OTHER PUBLICATIONS

Choo, H. P. 2001. Journal of Materials Chemistry 11:2906.*

Choo, H. P. 2001. Journal of Molecular Catalysis A: Chemical 165:127.*

Choo, H. P. 2003. Journal of Molecular Catalysis A: Chemical 191:113.*

International Search Report for PCT/NL05/000347 dated Dec. 30, 2005.

A. Behr. Selektive Haertung Mehrfach Ungesaettigter Fettsaeuren in Der Fluessigphase. Fett—Lipid.Fat Science Technology, 19930101 Wiley-VCH Verlag,Weinheim, DE. vol. 95,Nr:1,pp. 2-12.

V. B. Ukraintsev, et al. Hydrogenation of vegetable oils in the presence of carbon-supported palladium nanoclusters. Russian Journal of General Chemistry, 2010, vol. 80, No. 4, pp. 866-867.

L N. Lewis. Chemical Catalysis by Colloids and Clusters. Chemical Reviews, 19931201 ACS, Washington, DC, US. vol. 93,Nr:8,pp. 2693-2730.

N. Toshima, et al. Colloidal Dispersions of Platinum and Palladium Clusters Embedded in the Micelles. Preparation and Application to the Catalysis for Hydrogenation of Olefins. Bulletin of the Chemical Society of Japan, 19920101 Chemical Society of Japan, Tokyo, JP. vol. 65,Nr:2,pp. 400-409.

S. Narayanan, et al. Structural influence of hydroxytalcite on Pd dispersion and phenol hydrogenation. Chemical Communications—CHEMCOM, 19970101 Royal Society of Chemistry, GB. pp. 1991-1992.

J. C. A. A. Roelofs, et al.. First example of high loaded polymer-stabilised nanoclusters immobilized on hydrotalcite: effects in alkyne hydrogenation. Chemical Communications—CHEMCOM, 20040316 Royal Society of Chemistry, GB. pp. 970-971.

G. Mangnus, et al. Hydrogenation of Oils At Reduced TFA Content. Oils and Fats International, 20040701 International Trade Publications, Redhill, GB. pp. 33-35.

Translation of Office Action for Japanese patent application No. 2008-511065, dated Sep. 21, 2011.

H.P. Choo, et al. Hydrogenation of palm olein catalyzed by polymer stabilized Pt colloids. Journal of Molecular Catalysts: A Chemical. 2001, vol. 165, pp. 127-134.

* cited by examiner

*Primary Examiner* — Carolyn Paden
(74) *Attorney, Agent, or Firm* — Bernard Lau

(57) ABSTRACT

The invention is directed to a process for the hydrogenation of unsaturated triglycerides in the presence of a supported precious metal catalyst and hydrogen, in which process a precious metal catalyst is used, comprising an aggregate of solid support, precious metal nano particles and surfactant or polymer.

13 Claims, No Drawings

PROCESS FOR THE HYDROGENATION OF UNSATURATED TRIGLYCERIDES

BACKGROUND OF THE INVENTION

The invention is directed to a process for the hydrogenation of unsaturated triglycerides, such as edible oils, to produce partially saturated triglycerides (oils/fats), as well as to hydrogenated edible oils obtainable by such as process.

It is known to prepare partially hydrogenated triglycerides, especially hardened fats for use in cooking and frying fat, bread spread, such as margarine, and products having a lower fat content, or frying oils and lubricants from triglyceride, i.e. vegetable oil, such as soybean oil or rapeseed oil, by catalytic hydrogenation in the presence of hydrogen. This hydrogenation is necessary, among other reasons, to increase the oxidation stability (decrease of the amount of linolenic acid) and to obtain the desired melting behavior of the triglyceride, for instance for the purpose of obtaining sufficient spreadability. Hydrogenation can take place utilizing conventional hydrogenation catalysts, such as nickel or precious metal catalysts. The triglycerides used herein are poly-unsaturated, mainly based on C12 to C22 fatty acid moieties. The majority of the fatty acid moieties is formed by the C16 and C18 fatty acids The hydrogenation generally results in mono- or di-unsaturated fatty acid moieties in the triglyceride.

As consumer awareness of the health hazards of the use of products obtained by hydrogenation grows, so grows the desire to reduce as far as possible the content of trans-isomers in the unsaturated fatty acids. In the natural products, the cis-isomer occurs predominantly. Besides hydrogenation also isomerization usually occurs, resulting in the formation of trans-isomers. In the conventional catalytic hydrogenation of soybean oil to form a product having a content of completely saturated fatty acids of from about 12 to 14% (iodine value of about 70), in addition to the amount naturally present therein (generally about 15 wt. %) an increase of the trans-isomer content of about 30-50% is obtained. Typical reaction conditions herein comprise the use of a conventional nickel hydrogenation catalyst, a temperature of between 175 and 200° C. and 0.7 to 2 bar hydrogen pressure. In the non-food applications of partially hydrogenated triglycerides, such as lubricants, the presence of trans-isomers is less preferred because of the increased melting point of trans-isomers. It is to be noted that some pre-treatments of poly)unsaturated triglycerides, such as cleaning or decoloration, may lead to a small degree of isomerization. This usually accounts for the presence of about 0.5 to 2 wt. % of trans-isomers in the triglyceride prior to being subjected to hydrogenation.

The method for preparing partially saturated fatty acid-triglycerides with a low trans-isomer content has already been investigated extensively. One approach consists in adjusting the hydrogenation conditions, whereby hydrogenation is promoted in relation to isomerization by the use of much hydrogen at the surface of the catalyst. This means that it is required to work at a low temperature, at a high hydrogen partial pressure and with a proportionally slight amount of catalyst in relation to the amount of component to be hydrogenated. With this method it is possible to lower the trans-isomer content to about 10%, the saturated fatty acid content increase being about 15%. However, this method is commercially little attractive, because major capital investments would have to be made to achieve higher pressures.

It is also known to use supported precious metal catalysts for the hydrogenation of triglycerides. These catalysts have the property that they produce too much fully saturated fatty acid moieties. A review of the problems and possibilities of reducing trans-isomer formation is given in "Hydrogenation of oils at reduced TFA content" in Oils & Fats International, July 2004 (pages 33-35).

It would be very attractive to have a precious metal catalyzed hydrogenation process for unsaturated triglycerides, which process produces hydrogenated triglycerides having reduced amounts of trans-isomers and saturates, compared to conventional hydrogenation processes.

BRIEF SUMMARY OF THE INVENTION

Accordingly it is an object of the invention to provide a process for the hydrogenation of triglycerides, i.e. of edible oils, which does not possess the above-mentioned disadvantages or does so to an appreciably lesser extent.

In the first embodiment the invention provides a process for the hydrogenation of polyunsaturated edible oils in the presence of a supported precious metal catalyst and hydrogen, in which process a precious metal catalyst is used, comprising an aggregate of solid support, precious metal nano particles and surfactant or polymer.

Surprisingly it has been found, that the aggregate of the support, the nano-particles, and the polymer and/or surfactant, provides a catalyst that is active in the hydrogenation of edible oils, while at the same time leading to low amounts of isomerization products and producing only low amounts of additional saturates.

In a second embodiment the invention is directed to unsaturated hydrogenated edible oils, such as shortenings or frying oils, which are obtainable by the process of the invention. Such hydrogenated edible oils, preferably soybean oil, are characterised by a combination of iodine value, amount of trans-isomers, which is low for hydrogenated edible oils and solid fat contents at 10 and 35° C., the $SC_{10}$ and $SC_{35}$, as defined in the AOCS method for determining the solid fat content (rev 1997).

DETAILED DESCRIPTION OF THE INVENTION

These hydrogenated oils specifically are characterized by the presence of an amount of trans isomers, which is intermediate between the original value of trans-isomers in the material to be hydrogenated, generally about 0.5 to 2 wt. %, and the value that is obtained using a hydrogenation process according to the present state of the art.

More specifically, these hydrogenated edible oils are characterized by having a iodine value between 60 and 80, an amount of trans isomers which is at most 9 wt. %, but not less than 2.5 wt. %, an $SC_{10}$ between 39 and 47 g/100 g and an $SC_{35}$ of at most 15 g/100 g, preferably between 2 and 15 g/100 g. These products are suitable for use as shortening and in margarines.

Hydrogenated frying oils are characterised by a combination of iodine value and composition.

Another embodiment of the invention accordingly concerns frying oils, which are characterised by an iodine value of at least 80, a content of trans isomers of between 0.5 and 5.0, in some situations between 2.0 and 5.0 wt. %. Further it is preferred that the amount of linolenic acid is as low as possible, preferably below 5 wt. %, more preferred below 3 and with the most preference below 2 wt. %.

In the process of the present invention an important aspect is the choice of the specific catalyst. In this catalyst the precious metal is present as elementary nano-particles, that means particles of a size of 1 to 12 nm, which are particles that exist as such in a solution, without support. The catalyst consist of an aggregate of three components. The first aspect of the aggregate is the combination of nano-particles and the polymer and/or surfactant. The nature of the aggregate or clusters is not clearly understood; it may be that the particles are bonded together by the polymer and/or surfactant; it is also possible that the polymer and/or surfactant provides some sort of coating, or that the polymer and/or surfactant acts as a shielding between the nano-particles to produce clustered nano-particles. The size of the clusters is generally between 12 and 40 nm.

The second aspect is the combination of the nano-particles and the polymer and/or surfactant with the support. Here also, the mechanism is not understood. It has, however, been observed, that the aggregate forms a stable heterogeneous catalyst, which can be used very advantageously in the hydrogenation of unsaturated triglycerides. The nature of the adherence is not known; it could be one of the mechanisms described above in relation to the nano-particles.

In the present invention, the catalyst is produced using a method, which comprises reducing a precious metal precursor dissolved in a solution also containing a surfactant and/or a polymer, which solution may further contain a dispersed support material. Because of the reduction in the presence of the surfactant and/or polymer during the reduction aggregates of nano-particles and the surfactant and/or polymer are formed. These aggregates may be nano-particles or clustered nano-particles. In case no support was present during the reduction, the solution containing the nano-particles is combined with a support material, preferably as a slurry in water. This results in aggregates of the (clustered) nano-particles, support and the polymer and/or surfactant.

Generally the amount of precious metal in the aggregates is between 0.01 and 10.0 wt. % calculated on the weight of the aggregate material, preferably between 0.1 and 5.0 wt. %.

The precious metal may be selected from the group consisting of platinum, palladium, iridium, rhodium, ruthenium, gold, silver and combinations thereof, preferably platinum. The hydrogenation of the precious metal ions to metal can be carried out in any suitable way, as known for the reduction of precious metal salts to precious metal. Examples are the use of hydrogen or reducing materials dissolved together with the precious metal salt, followed by heating, if necessary. Examples of reducing compounds are ethylene glycol, $NaBH_4$, formiate and the like.

The support material may be any material that is suitable as support for hydrogenation of edible oils, more in particular soybean oil. A requirement thereof is that the support does not dissolve in the oil. This requirement is for example met by carbon and the well known oxidic materials, such as silica, alumina, zirconia, titanium oxide, zinc-oxide and the like, but it is also possible to use molecular sieve materials and (synthetic) clays.

Although the mechanism is not entirely clear, it is assumed, that the polymer and/or surfactant plays an important role in maintaining the aggregate structure. It is also possible, that this is the determining factor in obtaining the nano-particle clusters. Suitable polymers and surfactants are those materials that promote the formation of the clusters and aggregates. Preferred examples are the polymers based on a carbon-chain, further containing hetero atoms, such as N, S or O, which may provide coordinating activity towards the metal atoms in the nano-particles and/or during the hydrogenation. More in particular preference is given to those polymers that contain a ring-structure as side group, more in particular an aromatic or aliphatic ring with at least one hetero-atom, preferably nitrogen. Most preferred is the use of PVP (polyvinyl pyrrolidone) as this provides the best results In case a surfactant is used, preference is given to surfactants of the cationic, anionic or non-ionic-types or with polyalcohols, such as di(hydrotallow)dimethylammoniumchloride, tradename Arquad 2HT-75 surfactant (cationic), 3-chloro-2-hydroxypropyldimethyl-dodecylammonium chloride, tradename Quab 342, lauryldimethylcarboxymethylammonium betaine, tradename Rewoteric AM DML surfactant (anionic), Na-cocoamidoethyl-N-hydroxyethylglucinate, tradename Dehyton G surfactant (non-ionic), decaethylene glycol hexadecyl ether, tradename Brij 56 surfactant (non-ionic), polyethylene glycol dodecyl ether, tradename Brij 35 surfactant (non-ionic), polyoxyethylene sorbitane monolaurate, tradename Tween 20 surfactant (non-ionic), polyoxyethylene sorbitane monopalmitate, tradename Tween 40.

The amount of polymer and/or surfactant in the final aggregate may vary widely. Suitable amounts are in the same order of magnitude as the amount of precious metal, or higher. This leads thereto that the amounts are between 0.1 and 15 wt. % calculated on the weight of the aggregate.

One catalyst that may be used in the present invention has been described in Roelofs et al, Chem Commun., 2004, pages 970-971. This document describes the production of polyvinyl pyrrolidone stabilised Pd-nanoclusters, supported on hydrotalcite supports.

The hydrogenation of the edible oils, preferably soybean oil can be done in the manner that is usual in the art. Temperature, duration and hydrogen pressure can be suitably selected to take into account the required iodine value and amount of trans isomers. In general the temperature will be between 30 and 200° C., the hydrogen pressure between 1 and 200 bar(a) and the duration will vary between 5 min and 4 hours. In general will higher temperature, higher hydrogen pressures and a longer duration, lead to lower iodine values.

The catalyst is preferably slurried into the edible oil and after the hydrogenation has been completed, removed by filtration. It is also possible to use a fixed bed or loop reactor containing the catalyst in fixed form. The amount of catalyst, based on precious metal, is preferable between 5 and 500 ppm.

The invention is now elucidated on the basis of examples.

1. Preparation of a Nano-Pt Silica Supported Catalyst

In a typical experiment, 3 gram PVP was dissolved in 75 g ethylene glycol.

To this solution, 20.2 g of a 3.13% tetra ammine Pt nitrate solution (calculated as PT) was added. This Pt-containing solution was heated for 55 sec in a 750 W laboratory microwave. The solution coloured from clear orange to a black suspension indicating the reduction of the Pt from ionic to zerovalent.

This hot solution was added to a suspension of 12 g silica powder (particle size of 30 micrometer, 480 m2/g and a pore volume of 1.1 ml/g) in 200 ml deionised water. After agitation for 16 h, the product was washed, filtered and dried at 110° C. A silica supported Pt catalyst was obtained which contained a Pt-loading of 1.3% Pt. Transmission electromicroscopy (TEM) photographs revealed a particle size distribution of 2 to 7 nm for the Pt-nano particles and a particle size distribution of 14 to 40 nm for the nano-particle clusters.

2. Hydrogenation of Soybean Oil to Produce a Low-Trans Shortening with an IV of 70.

In a typical experiment, 50 g of Refined Bleached and Deodorised soybean oil was hydrogenated at a hydrogen pressure of 4 barg and a temperature of 50° C. with the nano-Pt silica supported catalyst of example 1, containing 1.3% Pt. The composition of the original oil was: 10.5 wt % C16:0, 4.3 wt % C18:0, 23.9 wt % C18:1, 51.1 wt % C18:2, 6.4 wt % C18:3 and a total trans-isomers of 2.2 wt %. The amount of catalyst applied was 50 ppm based on the amount of precious metal. The hydrogenation was carried out until the amount of hydrogen that was consumed corresponded with a IV level of 70. The oil composition at this IV of 70 was determined at: 10.6 wt % C16:0, 25.9 wt % C18:0, 39.8 wt % C18:1, 16.9 wt % C18:2, 0.7 wt % C18:3 and a total trans-isomers of 4.5 wt %. The Solid Fat Curve as measured by low-resolution NMR (AOCS method rev. 1997) of this oil product gave the following characteristics: 43% solids at 10° C.; 33% solids at 20° C.; 20% solids at 30° C.; 13% solids at 35° C., and 8% solids at 40° C.

3. Hydrogenation of Soybean Oil to Produce a Low-Trans Frying Oil with an IV of 110.

In a typical experiment, 50 g of Refined Bleached and Deodorised soybean oil was hydrogenated at a hydrogen pressure of 4 barg and a temperature of 50° C. with the nano-Pt silica supported catalyst of example 1, containing 1.3% Pt. The composition of the original oil was: 10.5 wt % C16:0, 4.3 wt % C18:0, 23.9 wt % C18:1, 51.1 wt % C18:2, 6.4 wt % C18:3 and a total trans-isomers of 2.2 wt %. The amount of catalyst applied was 50 ppm based on the amount of precious metal. The hydrogenation was carried out until the amount of hydrogen that was consumed corresponded with a IV level of 110. The oil composition at this IV of 110 was determined at: 10.6 wt % C16:0, 9.9 wt % C18:0, 29.3 wt % C18:1, 41.1 wt % C18:2, 2.9 wt % C18:3 and a total trans-isomers of 2.9 wt %.

The invention claimed is:

1. A method comprising:

hydrogenating polyunsaturated triglycerides in the presence of a supported precious metal catalyst and hydrogen, wherein the precious metal catalyst comprises an aggregate of solid support, precious metal nano particles and a polymer, wherein the precious metal nanoparticles are clusters of elementary nanoparticles, and wherein the precious metal nanoparticles have a size of about 1 to 12 nm and the clusters of the elementary nanoparticles have a size of 12 to 40 nm.

2. The method of claim 1, wherein the support is selected from a group of oxidic supports.

3. The method of claim 2, wherein the polymer is selected from a group of aromatic polymeric materials containing at least one hetero-atom in the aromatic group.

4. The method of claim 1, wherein the polymer is selected from a group of aromatic polymeric materials containing at least one hetero-atom in the aromatic group.

5. The method of claim 1, wherein the polymer is selected from a group of polymeric materials consisting of polyvinyl pyrolidone.

6. The method of claim 1, wherein the precious metal is selected from at least one of platinum, palladium, iridium, rhodium, ruthenium, silver, or gold.

7. The method of claim 6, wherein the amount of precious metal is between 0.01 and 10 wt. %.

8. The method of claim 6, wherein the triglyceride is an edible oil.

9. The method of claim 1, wherein the amount of precious metal is between 0.01 and 10 wt. %.

10. The method of claim 1, wherein the triglyceride is an edible oil.

11. The method of claim 1, wherein the triglyceride contains an amount of linolenic acid.

12. The method of claim 1, wherein the linolenic acid is hydrogenated to mono or di-unsaturated compounds.

13. The method of claim 1, wherein the catalyst is obtained by a process comprising:

reducing precious metal ions to precious metal clusters in the presence of the bonding polymer; and contacting the precious metal clusters are contacted with the support.

* * * * *